United States Patent [19]
Snyder et al.

[11] Patent Number: 5,851,804
[45] Date of Patent: Dec. 22, 1998

[54] CHIMERIC KANAMYCIN RESISTANCE GENE

[75] Inventors: Linda Anne Snyder, Pottstown; C. Satishchandran, Lansdale, both of Pa.

[73] Assignee: Apollon, Inc., Malvern, Pa.

[21] Appl. No.: 642,045

[22] Filed: May 6, 1996

[51] Int. Cl.$^6$ .......................... C12P 19/34; C07H 21/04; C12N 15/54; C12N 15/63

[52] U.S. Cl. .................. 435/91.1; 435/172.3; 435/252.3; 435/320.1; 514/44; 536/23.1; 536/23.2; 536/23.6; 536/23.7

[58] Field of Search .............................. 435/91.1, 172.3, 435/320.1, 252.3, 252.33; 514/44; 536/23.1, 23.2, 23.6, 23.7

[56] References Cited

U.S. PATENT DOCUMENTS

| | | | |
|---|---|---|---|
| 4,727,028 | 2/1988 | Santerre et al. | 435/356 |
| 4,945,050 | 7/1990 | Sanford et al. | 435/172.1 |
| 5,036,006 | 7/1991 | Sanford et al. | 435/170.1 |
| 5,593,972 | 1/1997 | Weiner et al. | 514/44 |

FOREIGN PATENT DOCUMENTS

| | | |
|---|---|---|
| WO 90/11092 | 10/1992 | WIPO . |
| WO 93/17706 | 9/1993 | WIPO . |
| WO 93/23552 | 11/1993 | WIPO . |
| WO 94/16737 | 8/1994 | WIPO . |

OTHER PUBLICATIONS

PCT International Search Report dated Aug. 21, 1997, 1 page.

Deng et al., "Simultaneous randomiztion of antibody CDRs by a synthetic ligase chain reaction strategy", *Nucl. Acids Res.*, 1993, 21(18), 4418–4419.

Pachuk et al., "Chain reaction cloning: A novel cloning strategy", *FASEB J.*, 1996, 10(6), A1127, abstract No. 740.

Rouwendal et al., "Simultaneous mutagenesis of multiple sites: Application of the ligase chain reaction using PCR products instead of oligonucleotides", *Biotechniques*, 1993, 15(1), 69–71, 73–75, and 77.

PCT International Search Report dated Aug. 27, 1997, 1 page.

Hoshino et al., "Determination of the transcriptional initiation sites of the kanamycin resistance genes of pUB110 and pTHN1", *J. Ferment. Bioeng.* 79(1): 62–63, 1995.

McKenzie et al., "The nucleotide sequence of pUB110: some salient features in relation to replication and its regulation", *Plasmid* 15 (2):93–103, Mar. 1986.

Holmes, D. et al., "Cloning of an Aminoglycoside–Resistance–Encoding Gene, KamC, from *Saccharopolyspora hirsuta*: Comparison with KamB from *Streptomyces tenebrarius*", *Gene* 1991, 102, 19–26.

Kües, U. and Stahl, "Replication of Plasmids in Gram–Negative Bacteria", *Microbiological Reviews* 1989, 53(4), 491–516.

Matsumura, M. et al., "Enzymatic and Nucleotide Sequence Studies of a Kanamycin–Inactivating Enzyme Encoded by a Plasmid from Thermophilic Bacilli in Comparison with That Encoded by Plasmid pUB110", *J. of Bacteriol.* 1984, 160(1), 413–420.

Oka, A. et al., "Nucleotide Sequence of the Kanamycin Resistance Transposon Tn903", *J. Mol. Biol.* 1981, 147, 217–226.

Sadaie, Y. et al., "Purification and Characterization of a Kanamycin Nucleotidyltransferase from Plasmid pUB110–Carrying Cells of *Bacillus subtilis*", *J. of Bacteriol.* 1980, 141(3), 1178–1182.

Satishchandran, C. et al., "Novel *Escherichia coli* K–12 Mutants Impaired in S–Adenosylmethionine Synthesis", *J. of Bacteriol.* 1990, 172(8), 4489–4496.

Schwotzer, U. et al., "R–Plasmid Mediated Aminoglycoside Resistance in *Staphylococcus epidermidis*: Structure Determination of the Products of an Enzyme Nucleotidylating the 4'– and 4"–Hydroxyl Group of Aminoglycoside Antibiotics", *FEMS Microbiology Letters* 1978, 3, 29–33.

Shaw, K.J. et al., "Correlation between Aminoglycoside Resistance Profiles and DNA Hybridization of Clinical Isolates", *Antimicrobial Agents and Chemotherapy* 1991, 35(11), 2253–2261.

Shaw, K.J. et al., "Molecular Genetics of Aminoglycoside Resistance Genes and Familial Relationships of the Aminoglycoside–Modifying Enzymes", *Microbiol. Reviews* 1993, 57(1), 138–163.

Siregar, J. et al., "Purification, Characterization, and Investigation of the Mechanism of Aminoglycoside 3'– Phosphotransferase Type Ia", *Biochemistry* 1995, 34, 12681–12688.

Wingard, Jr. L. et al., "Inhibitors of Bacterial Ribosomal Actions", Chap. 47 in Human Pharmacology Molecular–to–Clinical, Mosby Year Book, St. Louis, 1991, pp. 659–676.

*Primary Examiner*—Jasemine C. Chambers
*Assistant Examiner*—Scott D. Priebe
*Attorney, Agent, or Firm*—Woodcock Washburn Kurtz Mackiewicz & Norris LLP

[57] ABSTRACT

Chimeric kanamycin resistance genes are disclosed. The chimeric genes comprise a nucleotide sequence that encodes ANT(4')-IA enzyme operably linked to a heterologous promoter and a heterologous termination sequence. Plasmids that comprise the chimeric kanamycin resistance gene are disclosed. Bacterial cells that comprise the chimeric gene on a plasmid or integrated into the bacterial genome are disclosed. Methods of producing plasmids are disclosed. Pharmaceutical compositions comprising plasmids that include the chimeric genes are disclosed. Methods of enhancing growth of a bacterial cells are disclosed. Plasmid which comprise the chimeric kanamycin resistance gene and the sequences from herpes simplex virus gene HSVgD$_2$ or human immunodeficiency virus are disclosed.

29 Claims, 8 Drawing Sheets

```
CAGTAATACAAGGGGTGTT | GTG AAT GGA CCA ATA A...
                      M   N   G   P   I
                      ATG GAC CAA TAA...
                      M   D   Q   *
```
FIG.2
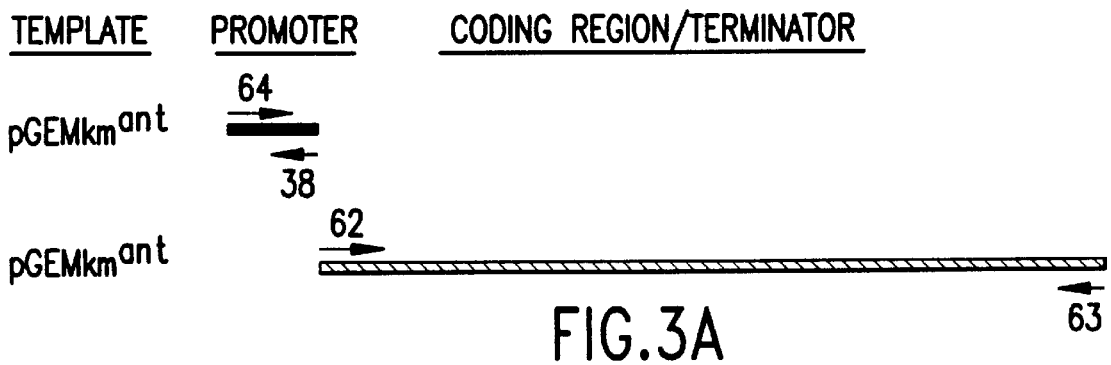
FIG.3A
FIG.3B

```
MPV64      MPV37
       20        40        60        80       100
       .         .         .         .         .
GCTCTAGAGGCCCGGCCGGGAAAGCCACGTTGTGTCTCAAATCTCTGATGTTACATTGCACAAGATAAAATATATCATCATGAACAATAAAACTGTCT
CGAGATCTCCGGCCGGCCCCTTTCGGTGCAACACAGAGTTTAGAGACTACAATGTAACGTGTTCTATTTTATATAGTAGTACTGTTATTTTGACAGA

MPV39           160      MPV62
      120       140       .         .         200
       .         .                            .
GCTTACATAACAGTAATACAAGGGGTGTTATGAACGGACCAATAATAATGACTAGAGAAGAAGAATGAAGATTGTTCATGAAATTAAGGAACGAATAT
CGAATGTATTGTCATTATGTTCCCCACAATACTTGCCCTGGTTATTATTACTGATCTCTTCTTCTTCTTACTTCTAACAAGTACTTTAATTCCTTGCTTATA

MPV38
      220       240       260       280       300
       .         .         .         .         .
TGGATAAATATGGGATGATGTTAAGGCTATTGGTGTTATGGCTCTCTTGGTCGTCAGACTGATGGGCCCTATTCGGATATTGAGATGATGTGTCAT
ACCTATTTATACCCTACTACAATTCCGATAACCAGAGAACAGTCTGACTACCCGGGATAAGCCTATACTCTACTACACAGTA 320       340       360       380       400
       .         .         .         .         .
GTCAACAGAGGAAGCAGAGTTCAGCCATGAATGACACCGGTGAAGGTGAAGTGAATTTGATAGCGAAGAGATTCTACTAGATTATGCATCT
CAGTTGTCTCCTTCGTCTCAAGTCGGTACTTACCGTTGGCCACTGTGTACCGGTACCTTCCACCTTCTCTAAGATGATCTAATACGTAGA 420       440       460       480       500
       .         .         .         .         .
CAGGTGGAATCAGATTGGCCCGCTTACACATGTCAATTTTTCTCTATTTTGCCGATTTATGATTCAGTGGATACTTAGAGAAAGTGTATCAAACTGCTA
GTCCACCTTAGTCTAACCGGGCGAATGTGTACCAGTTAAAAGAGATAAACGGCTAAATACTAAGTCCACCTATGAATCTCTTTCACATAGTTTGACGAT 520       540       560       580       600
       .         .         .         .         .
AATCGGTAGAAGCCCAAACGTTCCACGATGCGATTGTGCCCTATCGTGAGAAGAGCTGTTTGAATATGCAGGCAAATGGCTAATATTCGTGTGCAAGG
TTAGCCATCTTCGGGTTTGCAAGGTGCTACGGTTGCAAGGTGCTAAACACGGAATAGCATCTTCTGACAACTTATACGTCCGTTTACCGATTATAAGCACACGTTCC
```

Figure 4A

CHIMERIC KANAMYCIN RESISTANCE GENE

FIELD OF THE INVENTION

The present invention relates to chimeric kanamycin resistance genes and methods of making and using the same. The chimeric kanamycin resistance genes of the invention can be used to confer to host cells, including gram negative bacteria, resistance to a narrow spectrum of antibiotics including kanamycin.

BACKGROUND OF THE INVENTION

DNA-based pharmaceutical agents are being developed as a new generation of therapeutics and vaccines. DNA therapeutics are typically plasmids that contain one or more genes which compensate for a genetic defect of a patient and/or encode a protein whose presence has a therapeutic effect on the patient. DNA vaccines are typically plasmids which contain one or more genes from a particular pathogen or undesirable cell. Once injected, the coding sequence of the DNA therapeutic vaccine is expressed in the patient or vaccinee as protein products. Examples of protocols for delivering DNA which can be adapted for use with the present invention are described in U.S. Pat. No. 4,945,050 issued Jul. 31, 1990 to Sanford et al., U.S. Pat. No. 5,036,006 issued Jul. 30, 1991 to Sanford et al., PCT publication Ser. No. WO 90/11092, PCT publication Ser. No. WO 93/17706, PCT publication serial number WO 93/23552, and PCT publication Ser. No. WO 94/16737 which are each incorporated herein by reference.

Clinical vectors useful as part of DNA-based agents have backbones which comprise elements for their manufacture and elements which drive expression of the desired protein or immunogen once the plasmid is injected into the individual. For expression of the desired protein or immunogen in the individual, a eukaryotic promoter, a polylinker for insertion of a gene encoding an desired protein or immunogen, and a polyadenylation signal are provided. To minimize the chances of integration of the plasmid into host cellular DNA, the plasmid preferably does not contain retroviral LTRs, eukaryotic origins of replication, known oncogenes, nor any sequences with known homology to human DNA. A bacterial origin of replication and an antibiotic selection gene are included to be used in the manufacturing of the agents. The most common antibiotic resistance gene is a kanamycin resistance gene such as the aph(3')-Ia gene.

The aph(3')-Ia gene is used to select for the plasmid during production in the presence of media containing kanamycin. Kanamycin is a member of the family of antibiotics known as aminoglycosides which have been in use for the last fifty years. Structurally, aminoglycosides are comprised of amino sugars linked by glycosidic bonds to an aminocyclitol ring (Wingard, L. B., et al., *Human Pharmacology: Molecular-to-Clinical* 1991, 659–676, which is incorporated herein by reference). These drugs are either bactericidal or bacteriostatic, and are known to interfere with protein synthesis. Although aminoglycosides are effective against gram negative and gram positive organisms, they are now prescribed less frequently because of their toxicity (small therapeutic index) and the development of bacterial resistance. Over time, bacterial strains have acquired resistance to this class of antibiotics, inactivating the drugs by novel enzymes which either phosphorylate, adenylate, acetylate, or methylate the drugs (Shaw, K. J., et al., *Microbiol Reviews* 1993, 57:138–163, which is incorporated herein by reference; and Holmes, D. J. et al., *Gene* 1991, 102:19–26, which is incorporated herein by reference). The enzyme conferring resistance is typically active against several members of the drug family.

An example of an aph(3')-Ia gene which can be used in clinical vectors is derived from transposon Tn903 of *E. coli* (Oka, A., et al., *J Mol Bio.* 1981, 147:217–226, which is incorporated herein by reference) and encodes an aminoglycoside 3'-phosphotransferase. This enzyme phosphorylates and inactivates a variety of aminoglycoside antibiotics including but not limited to kanamycin, neomycin, gentamicin B, geneticin, and netilmicin (Siregar, J. J., et al., *Biochemistry* 1995, 34:12681–12688, which is incorporated herein by reference). Some of these antibiotics are still used to treat bacterial infections in patients. The fact that APH (3')-IA enzyme is active against so many aminoglycosides is not surprising since most phosphotransferases go through a phosphoenzyme intermediate which is very reactive. APH (3')-IA enzyme can phosphorylate aminoglycosides which are not in its reported spectrum of activity, and it can behave as an ATPase as shown by its ability to transfer phosphate to water.

It is of concern that the aph(3')-Ia gene is the gene most commonly identified in clinical bacterial isolates resistant to multiple aminoglycosides and is present in approximately 20% of resistant strains. If a clinical vector contains the aph(3')-Ia gene, it is possible that this gene could be acquired by bacteria in a injected person which could complicate treatment of infections. There is a need for clinical vectors with improved safety.

SUMMARY OF THE INVENTION

To improve the safety of clinical vectors, the aph(3')-Ia gene used in clinical vectors may be replaced with a kanamycin resistance gene characteristic of gram positive bacteria, the ant(4')-Ia gene. The ANT(4')-IA enzyme is an adenylyl 4'-nucleotidyltransferase type Ia, a less reactive enzyme which confers resistance to a much more limited number of clinically relevant aminoglycosides, especially when compared with APH(3')-IA enzyme.

The present invention relates to a chimeric kanamycin resistance gene which comprises the coding sequence of the ant(4')-Ia gene operably linked to heterologous promoter and termination sequences from a non-ant(4')-Ia gene. In some embodiments, the initiation codon of the ant(4')-Ia coding sequence is modified to convert a poorly recognized start codon to a well recognized start codon and to eliminate an out of frame start codon. The regulatory sequences of the chimeric kanamycin resistance gene are selected to support growth of the host cell to be cultured in media containing kanamycin or other antibiotics to which the ant(4')-Ia gene confers resistance; e.g. the ant(4')-Ia confers resistance to neomycin to which mammalian cells are known to be sensitive. The engineered gene displays a more limited range of activity against aminoglycosides, thereby offering a significant safety improvement over other kanamycin resistance genes.

The present invention relates to a chimeric kanamycin resistance gene which comprises the coding sequence of the ant(4')-Ia gene operably linked to a promoter and termination sequence from an aph(3')-Ia gene, wherein the ant(4')-Ia coding sequence has an initiation codon, that has been modified to convert an poorly recognized start codon to a well recognized start codon and to eliminate an out of frame start codon. The chimeric kanamycin resistance gene supports growth of *E. coli* in media containing kanamycin or certain other aminoglycoside antibiotics. The engineered gene displays a more limited range of activity against aminoglycosides, thereby offering a significant safety improvement over other kanamycin resistance genes.

The present invention relates to plasmid vectors which comprise the chimeric kanamycin resistance gene. In some embodiments, the invention relates to plasmid vectors which comprise the chimeric kanamycin resistance gene that includes the ant(4')-Ia gene operably linked to a promoter and termination sequence from an aph(3')-Ia gene. In some preferred embodiments, the ant(4')-Ia coding sequence of the chimeric kanamycin resistance gene has an initiation codon that has been modified to convert a poorly recognized start codon to a well recognized start codon and to eliminate an out of frame start codon.

The present invention relates to host cells which comprise plasmid vectors that include the chimeric kanamycin resistance gene. In some embodiments, the invention relates to bacterial host cells that include plasmid vectors which comprise the chimeric kanamycin gene that includes the ant(4')-Ia gene operably linked to a promoter and termination sequence from an aph(3')-Ia gene. In some preferred embodiments, the ant(4')-Ia coding sequence of the chimeric kanamycin gene has an initiation codon that is modified to convert a poorly recognized start codon to a well recognized start codon and to eliminate an out of frame start codon. In some preferred embodiments, the bacterial host cell is *E. coli*.

The present invention relates to methods of producing a plurality of copies of plasmid vectors comprising the steps of culturing, in media which contains kanamycin or another antibiotic to which the ant (4')-Ia gene confers resistance, host cells which comprise plasmid vectors that include the chimeric kanamycin resistance gene. In some preferred embodiments, the invention relates to methods of producing plasmid vectors comprising the steps of culturing, in media that contains kanamycin, bacteria which comprise plasmid vectors that include the chimeric kanamycin resistance gene that includes the ant(4')-Ia gene coding sequence operably linked to a promoter and termination sequence from an aph(3')-Ia gene. In some preferred embodiments, the ant(4') -Ia gene coding sequence of the chimeric kanamycin gene has an initiation codon that is modified to convert a poorly recognized start codon to a well recognized start codon and to eliminate an out of frame start codon. In some preferred embodiments, the bacterial host cell is *E. coli*.

The present invention relates to pharmaceutical compositions which comprise plasmid vectors that include the chimeric kanamycin resistance gene. In some preferred embodiments, the invention relates to pharmaceutical compositions which comprise plasmid vectors that include the chimeric kanamycin resistance gene that include the ant(4') -Ia gene coding sequence operably linked to a promoter and termination sequence from an aph(3')-Ia gene. In some preferred embodiments, the ant(4')-Ia coding sequence of the chimeric kanamycin resistance gene has an initiation codon that is modified to convert a poorly recognized start codon to a well recognized start codon and to eliminate an out of frame start codon.

The present invention relates to treating individuals with pharmaceutical compositions which comprise plasmid vectors that include the chimeric kanamycin resistance gene. In some preferred embodiments, the invention relates to treating individuals with pharmaceutical compositions which comprise plasmid vectors that include the chimeric kanamycin gene that includes the ant(4')-Ia coding sequence operably linked to a promoter and termination sequence from an aph(3')-Ia gene. In some preferred embodiments, the ant(4')-Ia coding sequence of the chimeric kanamycin resistance gene has an initiation codon that is modified to convert a poorly recognized start codon to a well recognized start codon and to eliminate an out of frame start codon.

The present invention relates to plasmids which comprise herpes simplex virus gene $HSVgD_2$ or the HIV gene env. The present invention relates to plasmids which comprise a chimeric kanamycin resistance gene of the present invention and either the HSV gene $HSVgD_2$ or the HIV gene env.

The present invention relates to pharmaceutical compositions that comprise plasmids which comprise herpes simplex virus gene $HSVgD_2$ or the HIV gene env. The present invention relates to pharmaceutical compositions that comprise plasmids which comprise a chimeric kanamycin resistance gene of the present invention and either the HSV gene $HSVgD_2$ or the HIV gene env.

The present invention relates to methods of immunizing an individual against HSV or HIV comprising administering to an individual, plasmids which comprise herpes simplex virus gene $HSVgD_2$ or HIV gene env. The present invention relates to methods of immunizing an individual against HSV or HIV comprising administering to an individual plasmids which comprise a chimeric kanamycin resistance gene of the present invention and either the HSV gene $HSVgD_2$ or the HIV gene env.

The present invention relates to methods of producing a plurality of copies of plasmid vectors which comprise a chimeric kanamycin resistance gene of the present invention and either the HSV gene $HSVgD_2$ or the HIV gene env. The method comprises the steps of culturing, in media which contains kanamycin, host cells which comprise plasmid vectors that include the chimeric kanamycin resistance gene.

BRIEF DESCRIPTION OF THE FIGURES

FIG. 1A shows the PCR strategy to amplify individual fragments from the indicated templates. The promoter fragment encompasses the promoter and the 5' untranslated region of the aph(3')-Ia gene present in pUC4K, including the Shine-Dalgarno sequence. The coding region fragments are derived from the ant(4')-Ia gene in pUB110; primer MPV40 alters the Eco47III site. The terminator fragment is also derived from the aph(3')-Ia gene in pUC4K. FIG. 1B shows the CRC strategy to link the four PCR fragments as described in Example 1. After CRC was performed, some of the sample was amplified by PCR with MPV37 and MPV44.

FIG. 2 shows the sequence of the translation initiation region of the engineered ant(4')-Ia gene (SEQ ID NO:22). The vertical line indicates the junction generated by CRC between the promoter and coding region. The Shine-Dalgarno box is underlined. Two reading frames are shown: the upper reading frame SEQ ID NO:23 represents the desired sequence of the ant(4')-Ia gene but begins with GTG, while the lower SEQ ID NO:25 begins with ATG but is out of frame and terminates quickly (asterisk).

FIGS. 3A and 3B show the strategy to reconstruct the ant(4')-Ia gene as described in Example 1. FIG. 3A shows the PCR amplification of fragments from pGEMkm$^{ant}$. Primer MPV62 incorporates the base changes required to alter the first two codons. FIG. 3B shows the CRC strategy to link the two PCR fragments. After CRC was performed, some of the sample was subjected to PCR with MPV64 and MPV63.

FIGS. 4A and 4B show the DNA sequence of the chimeric kanamycin resistance gene (SEQ ID NO:3) generated according to Example 1. The initiation and stop codons are underlined and positions of the MPV primers are indicated.

FIG. 6A shows schematic diagrams of two plasmids: plasmid 19 and plasmid 24. FIG. 6B shows results from Western blots of RD cells transfected with plasmid 24 (lanes 2,3), plasmid 23 (lanes 4,5) and plasmid 19 (lanes 6,7) as described in Example 1. Lane 1 contains protein molecular weight markers, from top to bottom of blot: 175, 83, 62, 47.5, 32.5, 25, 16.5 and 6.5 kd in size.

DETAILED DESCRIPTION OF THE INVENTION

Figures 1A, 1B:
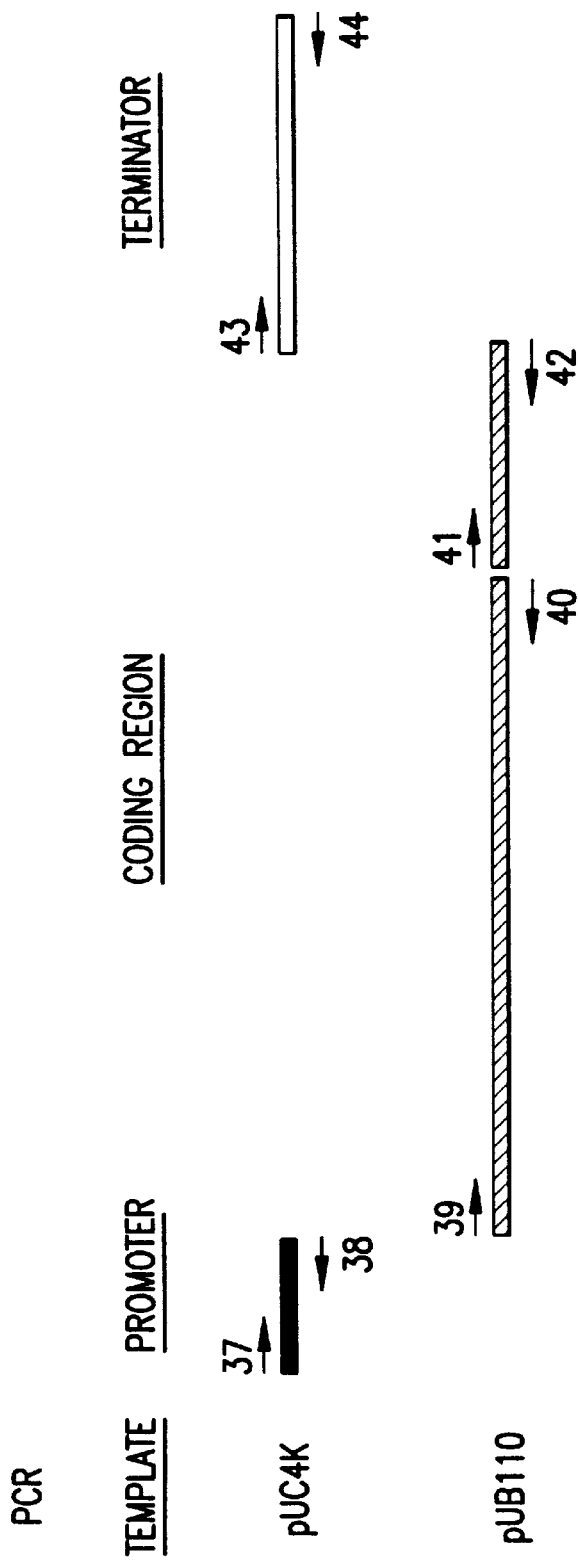
FIGS. 1A and 1B show the strategy used to construct the chimeric kanamycin resistance gene described in Example 1. Arrows indicate PCR primers or CRC bridge oligomers, with their MPV numbers (Table 1) indicated above or below.

As used herein, the term "chimeric kanamycin resistance gene" is meant to refer to an ant (4')-Ia gene coding sequence operably linked to non-ant (4')-Ia regulatory sequences.

As used herein, the term "ant (4')-Ia gene coding sequence" is meant to refer to nucleotide sequences that encode the ANT (4')-IA protein, such as for example the coding region for the ant (4')-Ia gene.

As used herein, the term "heterologous promoter" is meant to refer to a promoter from a non-ant(4')-Ia gene.

As used herein, the term "heterologous termination sequence" is meant to refer to a termination sequence from a non-ant(4')-Ia gene.

As used herein, the term "heterologous 5' untranslated region" is meant to refer to a 5' untranslated region from a non-ant(4')-Ia gene.

The purpose of an antibiotic resistance gene, such as the aph(3')-Ia kanamycin resistance gene, in clinical vector backbones is to enable selection for bacteria containing the plasmid during manufacturing. The antibiotic resistance gene contains a bacterial promoter to permit expression in bacteria, but it lacks a eukaryotic promoter, and therefore it cannot be expressed in human or mammalian cells. The aph(3')-Ia kanamycin resistance gene is commonly used in molecular biology gene constructs and is often included in clinical vector backbones as well.

Since the aph(3')-Ia gene is the aminoglycoside resistance gene most frequently identified in clinical isolates resistant to multiple antibiotics, the aph(3')-Ia gene confers resistance to a number of aminoglycosides that are still used in the clinic for the treatment of infections. It has been demonstrated that, because of the presence of these genes on mobile plasmids and transposons, antibiotic resistance genes are readily acquired by sensitive bacteria from resistant bacteria. Therefore, the use of pharmaceutical agents which contain that antibiotic resistance gene presents a safety concern since it is possible that sensitive bacteria in an injected person could acquire the aph(3')-Ia gene and thereby become aminoglycoside resistant.

In addition, the activity of APH(3')-IA enzyme also raises safety concerns. APH(3')-IA enzyme is a highly reactive phosphotransferase that can phosphorylate many substrates, including water. All aminoglycosides have 3' hydroxyl groups that could potentially serve as phosphate acceptors, and permit their inactivation. For example, although the aph(3')-Ia gene does not confer resistance to amikacin or butirosin A, the APH(3')-IA enzyme can still transfer phosphate to both. This substrate reactivity represents an evolutionary step toward detectable resistance against these antibiotics.

Ideally, the clinical vector used in DNA-based pharmaceutical agents contains an antibiotic resistance gene that does not confer resistance to aminoglycosides of clinical relevance, and is both less reactive and more specific in its choice of substrate.

The ANT(4')-IA gene product meets these criteria. First, the ant(4')-Ia gene confers resistance to a much smaller number of antibiotics than are inactivated by the APH(3')-IA enzyme. Second, the ANT(4') IA enzyme inactivates antibiotics by catalyzing the transfer of nucleotides to the 4' hydroxyl group of the substrate molecule (Sadale, Y., et al., J. Bacteriol. 1980, 141:1178–1182, which is incorporated herein by reference), a reaction whose rate is much slower and mechanistically more specific than that of the APH(3') -IA enzyme. In addition, only a few aminoglycosides have a 4' hydroxyl group to enable them to serve as substrates in such a reaction. The mechanistic specificity of the enzyme makes it very unlikely that the ANT(4')-IA enzyme would evolve into an enzyme with the ability to inactivate a broader spectrum of aminoglycosides.

The native coding sequence of the ant(4')-Ia gene is disclosed in Matsumura et al., J. Bacteriol. 1984 160:413–420, which is incorporated herein by reference.

The present invention provides a chimeric ant(4')-Ia gene that confers kanamycin resistance in manufacturing protocols which use E. coli as the bacterial host for plasmid production. The native ant(4')-Ia gene is derived from gram positive organisms. Its promoter, ribosome binding sites, and terminator are optimal for expression in gram positive bacteria, but not for gram negative E. coli (Miller, J. H., A Short Course in Bacterial Genetics 1992, Cold Spring Harbor Laboratory, Cold Spring Harbor, N.Y., which is incorporated herein by reference). The selectivity of gram negative promoters is due to the use of a single sigma factor versus the cascade of sigma factors required in gram positive organisms such as B. subtilis. In addition, gram negative bacterial ribosomes require that transcribed RNA contain signals for translation, which are lacking in RNA from gram positive organisms.

According to the invention, a chimeric kanamycin resistance gene is constructed to include the ant(4')-Ia gene coding sequences operably linked to non-ant(4')-Ia regulatory elements. Such non-ant(4')-Ia regulatory elements are necessary for efficient expression of functional ANT(4')-IA enzyme in E. coli. The ant(4')-Ia promoter and terminator are replaced with their counterparts from genes which express well in E. coli. The translation initiation region in the ant(4')-Ia gene is also modified.

The ant(4')-Ia gene coding sequence contains two potential start codons: an in-frame GTG and an out-of-frame ATG. Only translation from the GTG gives rise to a functional enzyme. However, GTG is unlikely to be recognized as the start codon by E. coli ribosomes and the out of frame ATG start codon is the more likely site for translation in E. coli. In view of this, the initiation codon and the immediately following codon were altered, from GTG AAT GGA (SEQ ID NO:1) to ATG AAC GGA (SEQ ID NO:2). Changing the bold-faced bases does not alter the protein sequence but the GTG start codon is converted to a new, more favored and efficient ATG start codon. The out of frame ATG start codon is eliminated.

As shown in FIGS. 1A and 1B, in some preferred embodiments, a chimeric kanamycin resistance gene is constructed to include ant(4')-Ia gene coding sequences operably linked to aph(3')-Ia regulatory elements. The ant (4')-Ia promoter and terminator are replaced with their counterparts from the original aph(3')-Ia gene, which expresses well in E. coli.

In some preferred embodiments, chimeric genes of the invention include the promoter and the 5' untranslated region, including the Shine-Dalgarno sequence, from the aph(3')-Ia gene.

In some preferred embodiments, an Eco47III site within the ant(4')-Ia coding region is eliminated for purposes of future cloning. In such embodiments, only a single base is altered and the protein sequence remains unchanged. This change requires the replacement of the T at nucleotide 697 with a G (FIG. 4).

Figure 4B:
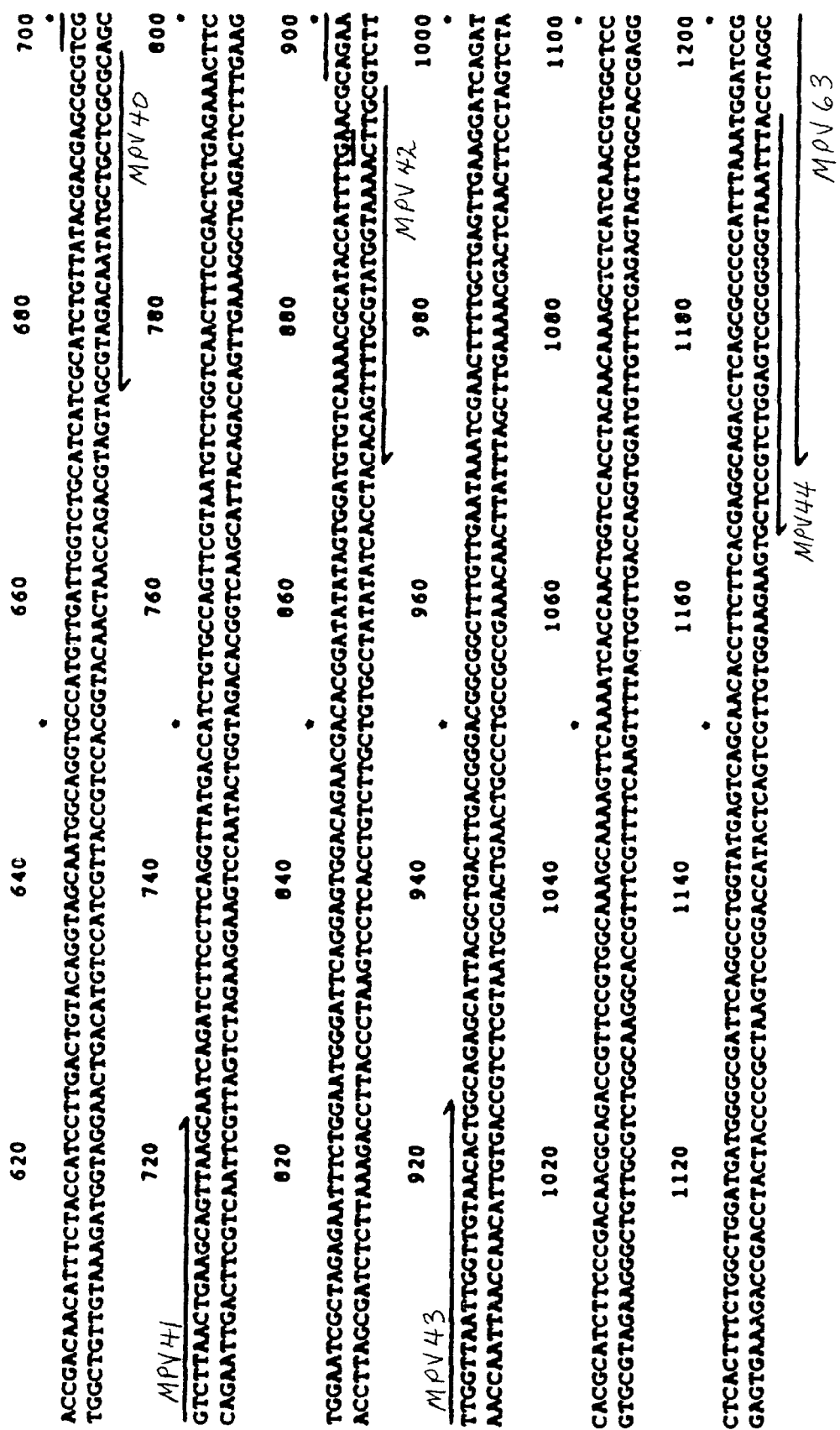

FIGS. 4A and 4B show the DNA sequence of a preferred embodiment (SEQ ID NO:3). In the depicted embodiment, the hybrid kanamycin resistance gene includes ant(4')-Ia gene coding sequences operably linked to the aph(3')-Ia promoter and the 5' untranslated region, including the Shine-Dalgarno sequence, and the terminator sequences. The initiation region of the ant(4')-Ia gene coding sequence is altered as described above to change the GTG start codon to an ATG start codon and to eliminate the out of frame ATG start codon.

Chimeric genes according to the present invention can be made by routine methods and readily available starting materials. Chimeric genes may be assembled from fragments of existing plasmids, produced synthetically using DNA synthesis technology or from a combination of fragments and synthesized DNA sequences.

The chimeric genes are useful to confer antibiotic resistance to bacteria such as E. coli. Accordingly, bacteria or other host cells carrying plasmids with the chimeric genes may be selected and cultured using media supplemented with kanamycin or another antibiotic to which the ant(4')-Ia gene confers resistance (see Table 2). The chimeric genes of the invention may be used in clinical vectors with enhanced safety relative to similar clinical vectors that have different kanamycin resistance genes. The clinical vectors of the invention may be provided with coding sequences of desired proteins or antigens and delivered to individuals as active agents in pharmaceutical compositions. Such pharmaceutical compositions may be used in methods of treating individuals therapeutically or prophylactically in gene therapy or genetic immunization protocols.

Bacterial promoters and 5' untranslated regions, including Shine-Dalgarno sequence, useful to form chimeric genes with the ant(4')-Ia coding sequences include, but are not limited to: the aph(3')-Ia gene promoter, the β-lactamase gene promoter, and the lacZ promoter.

Eukaryotic promoters and 5' untranslated regions, including a Kozak sequence, useful to form chimeric genes with the ant(4')-Ia coding sequences include, but are not limited to: the herpes simplex virus thymidine kinase gene promoter, the SV40 promoter, and the rat β-actin promoter.

In some preferred embodiments, the promoter used to form chimeric genes with the ant(4')-Ia gene coding sequences is the aph(3')-Ia gene promoter.

In some preferred embodiments, promoters and 5' untranslated regions including the Shine-Dalgarno sequence, useful to form chimeric genes with the ant(4')-Ia gene coding sequences are the aph(3')-Ia promoter and 5' untranslated regions.

Bacterial terminators useful to form chimeric genes with the ant(4')-Ia coding sequences include, but are not limited to: rho-dependent terminators, such as that from the aph(3') -Ia gene, and rho independent terminators, such as the ribosomal terminator rrnBT$_1$T$_2$.

Eukaryotic polyadenylation sequences useful to form chimeric genes with the ant(4')-Ia coding sequences include, but are not limited to: the SV40 polyadenylation signal, the herpes simplex virus thymidine kinase gene polyadenylation signal, and the bovine growth hormone polyadenylation signal.

In some preferred embodiments, the terminator sequence used to form chimeric genes with the ant(4')-Ia gene coding sequence is the aph(3')-Ia terminator sequence.

Vectors which can be provided with the chimeric kanamycin resistance gene include plasmids, DNA-based viral vectors such as adenovirus vectors, and RNA-based viral vectors such as retrovirus vectors. In addition, the chimeric kanamycin resistance gene can be integrated directly into the host cell genome such as integration into the chromosome of E. coli. An E. coli strain with the ant(4')-Ia gene integrated into the chromosome could be generated by homologous recombination. For example, the ant(4')-Ia gene can be inserted into the center of 1–2 kb of cloned E. coli DNA, and use the resulting linear fragment to transform E. coli (C. Satishchandran, et al., 1991 J. Bacteriol. 172:4489–4496, which is incorporated herein by reference).

Examples of plasmid vectors include, but are not limited to: plasmid 23, plasmid 24, plasmid 31, plasmid 41 and plasmid 28. Plasmid 23, shown in Example 5, is plasmid 4 with the ant(4')-Ia coding sequence inserted in place of the aph(3')-Ia coding sequence. Plasmid 4, shown in FIG. 5, contains a bacterial origin of replication, a composite promoter comprising the Rous sarcoma virus (RSV) enhancer in combination with the human cytomegalovirus (HCMV) intermediate early promoter, a polylinker/cloning site for insertion of coding sequence that encodes a desired protein or immunogen, an SV40 polyadenylation signal and the kanamycin resistance gene aph(3')-Ia. Plasmid 24 is plasmid 23 with the herpes simplex virus gene HSVgD$_2$ inserted into the cloning site of plasmid 23. The HSVgD$_2$ gene has also been inserted into plasmid 4 to produce plasmid 19. Plasmid 31 is plasmid 23 with a single point mutation in the bacterial origin of replication for the purpose of improving plasmid copy number and therefore DNA yield during fermentation. The mutation is the replacement of a C residue with a T residue. Plasmid 41 is plasmid 31 with the herpes simplex virus gene HSVgD$_2$ inserted into the cloning site of plasmid 31. Plasmid 28 is plasmid 23 with HIV genes env, rev, truncated nef, truncated vpu and the rev responsive element (rre) inserted into the cloning site of plasmid 23. HIV genes env, rev, truncated nef, truncated vpu and the rev responsive element (rre) have also been inserted into plasmid 4 to produce plasmid 3.

Cells which can contain the chimeric kanamycin resistance gene of the invention integrated into their chromosomal DNA or maintained in plasmid form include: gram negative bacteria, such as E. coli, Salmonella, Shigella; gram positive bacteria, such as Staphylococcus, Bacillus, Clostridium; eukaryotic cells, such as yeast, insect cells, animal cells and plant cells.

The present invention relates to plasmids which comprise herpes simplex virus gene HSVgD$_2$ or the HIV gene env including plasmids which comprise a chimeric kanamycin resistance gene of the present invention and either the HSV gene HSVgD$_2$ or the HIV gene env. In addition, the present invention relates to pharmaceutical compositions that comprise plasmids which comprise herpes simplex virus gene HSVgD$_2$ or the HIV gene env including pharmaceutical compositions that comprise plasmids which comprise a chimeric kanamycin resistance gene of the present invention and either the HSV gene HSVgD$_2$ or the HIV gene env.

The present invention relates to methods of immunizing an individual against HSV or HIV comprising administering to an individual, plasmids which comprise herpes simplex virus gene HSVgD$_2$ or the HIV gene env including immunizing an individual against HSV or HIV comprising administering to an individual plasmids which comprise a chimeric kanamycin resistance gene of the present invention and either the HSV gene HSVgD$_2$ or the HIV gene env and to methods of producing a plurality of copies of plasmid vectors which comprise a chimeric kanamycin resistance gene of the present invention and either the HSV gene HSVgD$_2$ or the HIV gene env. The method comprises the steps of culturing, in media which contains kanamycin, host cells which comprise plasmid vectors that include the chimeric kanamycin resistance gene.

According to the invention, plasmids encoding the HSV gene HSVgD$_2$ or the HIV gene env are particularly useful to practice aspects of the invention. Plasmids may generally comprise the elements as described in the genetic immunization patent applications U.S. Ser. No. 08/008,342, abandoned, 08/029,336 abandoned, 08/125,012, U.S. Pat. No. 5,593,972 and PCT application PCT/US94/00899, which are incorporated herein by reference, with the HSV gene sequence as described in U.S. Pat. No. 4,818,694 issued Apr. 4, 1989 to Watson et al. and U.S. Pat. No. 4,891,315 issued Jan. 2, 1990 to Watson et al. which are each incorporated herein by reference, or the HIV gene env described in Genetic Immunization patent applications. Such plasmids additionally include kanamycin resistance genes as described herein. Examples of plasmids which encode the HSV gene HSVgD$_2$ include plasmids 24 and 41, disclosed here. Examples of plasmids which encode the HIV gene env include plasmid 28, disclosed here.

EXAMPLES

Example 1

INTRODUCTION

Clinical vectors have been modified to replace the aph (3')-Ia gene with a chimeric kanamycin resistance gene. To compare the ability of either backbone to express eukaryotic genes, the envelope glycoprotein D gene (HSVgD$_2$) from herpes simplex virus 2 (HSV-2) was cloned into clinical vectors which had either one of the two kanamycin resistance genes. In tissue culture experiments, both vectors support expression of $HSVgD_2$ protein as detected by Western blot. Fermentation parameters of *E. coli* containing either vector were also compared. Growth of cells harboring the chimeric ant(4')-Ia gene was considerably enhanced when compared to cells harboring the aph(3')-Ia gene, although DNA yields per gram of cell were similar for either vector. The growth differences are most likely a consequence of the different biochemical requirements and activities of ANT(4')-IA enzyme and APH(3')-IA enzyme.

MATERIALS AND METHODS

Plasmids:

The kanamycin resistance gene aminoglycoside 3'-phosphotransferase type Ia (aph(3')-Ia) (Oka et al., 1981 Supra) was obtained from the plasmid pUC4K (Pharmacia, Piscataway, N.J.). This *E. coli* gene for resistance to kanamycin was originally derived from Tn903.

The kanamycin resistance gene adenylyl 4'-nucleotidyltransferase type Ia (ant(4')-Ia) (Matsumura et al., *J. Bacteriology* 1984, 160:413–420 which is incorporated herein by reference; Shaw et al., 1993 Supra) was obtained from the plasmid pUB110 (Sigma, St. Louis, Mo.). The pUB110 plasmid was originally discovered in gram positive *S. aureus*.

The clinical DNA vector is a plasmid backbone that contains a bacterial origin of replication, a composite promoter comprised of the Rous sarcoma virus (RSV) enhancer and the human cytomegalovirus (HCMV) immediate early promoter, a polylinker for insertion of a gene encoding a desired protein or antigen, an SV40 polyadenylation signal, and a kanamycin resistance gene. The original plasmid, plasmid 4, contains each of the elements described above and the kanamycin resistance aph(3')-Ia gene.

Plasmid 19 is the plasmid 4 vector with the HSV gene $HSVgD_2$ cloned between the promoter and polyadenylation signal.

Plasmid 23 is a modification of plasmid 4 in which the aph(3')-Ia gene is replaced with the chimeric ant(4')-Ia gene of the invention.

Plasmid 24 is plasmid 23 with the $HSVgD_2$ gene cloned between the promoter and polyadenylation signal.

Bacterial Strains:

*E. coli* DH10B ($F^-$ mcrA, Δ(mrr-hsdRMS-mcrBC) φ80dlacZΔM15 ΔlacX74 deoR recA1 endA1 araD139 Δ(ara,leu) 7697 galU galK λ-rpsL nupG) competent cells (Gibco-BRL, Grand Island, NY) were transformed according to the manufacturer's instructions with plasmid 4, plasmid 19, plasmid 23 and plasmid 24, and grown on LB plates containing 40 μg/ml kanamycin. Plasmid DNA was purified by the alkaline lysis procedure (Sambrook, S., et al., *Molecular Cloning*: A Laboratory Manual 1989, which is incorporated herein by reference). DH10B cells were transformed with $pBLUEkm^{ant}$ and pUC4K, in order to analyze the range of activity of ant(4')-Ia and aph(3')-Ia genes, respectively, against various aminoglycosides. These experiments were carried out by Microbiology Reference Laboratory, Cypress, Calif.

Primers and Bridge Oligomers:

DNA oligomers were designed for use in polymerase chain reaction (PCR) or in chain reaction cloning (CRC as described below), and were supplied by Research Genetics, Huntsville, Ala. Table 1 lists the primers and oligomers, and FIGS. 1A, 1B, 3A, 3B, 4A and 4B indicate their positions in relation to the templates and the final chimeric ant(4')-Ia sequence. PCR primers were stored as 100 μM stocks in sterile water, while bridge oligomers were stored at 1 mg/ml in sterile water.

PCR Reaction Conditions:

Reactions were performed in 50 μl volumes containing 1× PCR buffer (50 mM KCl, 10 mM Tris, pH 8.3, 1.5 mM $MgCl_2$, 0.001% gelatin), 200 μM each DNTP, 0.2 μM each primer, 1 unit AmpliTag® thermostable polymerase (Perkin-Elmer), and 5 ng of template DNA. Samples went through 30 cycles of 94° C. 1 minute, 72° C. 1–2 minutes in a Perkin Elmer 9600 machine.

During the first round of cloning, the engineered ant(4')-Ia gene was initially amplified to include FseI and SwaI sites at the 5' and 3' ends (primers MPV37 and MPV44), for use in future cloning experiments. When the gene was subjected to PCR to alter the first and second codons, XbaI and BamHI sites were additionally engineered onto the 5' and 3' ends of the gene (primers MPV64 and MPV63, respectively), to enable easy cloning into those same sites in pBluescript.

CRC Reaction Conditions:

Chain reaction cloning (CRC) employs a thermostable ligase to join DNA fragments in a desired order. It is often difficult to make gene constructs because DNA fragments lack either compatible restriction enzyme sites, or enzyme sites at the "right" places. This method obviates the need for such sites, because it joins fragments in a precise order determined by the experimenter. One need only know the sequence at the ends of the fragments to be joined. A "bridge" oligomer is designed which is identical to a desired junction region, and which overlaps the two fragments to be joined by approximately 20 to 25 bases on each side of the junction. The two fragments are incubated in equimolar ratios with an excess of the bridge oligo, and heated to 94° C. to melt the DNA strands. The sample is cooled to 68°–72° C., enabling the bridge oligo to hybridize to the single strands from the two fragments. The oligo brings together these single strands so that the ligase can join them together. This cycle is repeated many times, and in subsequent cycles both the bridge oligo and previously joined single strands act as templates for hybridization and ligation. Once CRC is completed, a portion of the sample is usually subjected to PCR, using primers derived from the ends of the joined fragments, and the amplified DNA can be cloned and analyzed.

CRC was employed to join four fragments in a specific order to generate the engineered ant(4')-Ia gene, while two fragments were joined by CRC to generate plasmid 23.

DNA fragments used in CRC were obtained through PCR or restriction digestion. In either case, the fragments were separated on low-melt agarose gels and purified (Sambrook et al., 1989 Supra) . Reactions were in 100 μl volumes containing equimolar amounts of the fragments to be ligated (up to 1 μg of each fragment), 8–10 picomoles of each bridge oligo, 1× CRC buffer (20 mM Tris, pH 8.3, 25 mM KCl, 10 mM $MgCl_2$, 0.5 mM NAD, 1% Triton X-100), and 50–100 units of Ampligase® (Epicentre, Madison, Wis.). Samples went through 50 cycles of 94° C. 1 minute, 68°–72° C. 2 minutes. When CRC products were to be resolved and amplified by PCR, approximately 5% to 40% of the CRC reaction was used as template for PCR.

Subcloning, Ligations and Transformations:

Some DNA fragments obtained by PCR amplification were ligated into the plasmid pCR™3, and the ligation products were used to transform *E. coli* one shot™ TOP10F' cells, according to the manufacturer's instructions (Invitrogen, San Diego, Calif.). The ant(4')-Ia engineered gene was initially cloned this way, to yield plasmid pkm23. The ant(4')-Ia gene was excised from pkm23 with XbaI and BamHI and subcloned into the same sites in pGEM11Zf+ for functional testing, to yield plasmid pGEMkm$^{ant}$. DNA from pGEMkm$^{ant}$ was the template for the reconstruction of ant(4')-Ia. After the altered gene was generated by PCR and CRC, it was cleaved at engineered XbaI and BamHI ends and subcloned into those sites in pBluescript, yielding pBLUEkm$^{ant}$.

The $HSVgD_2$ gene in plasmid 19 was excised from that plasmid with KpnI and MluI. The fragment was ligated into the same sites present in plasmid 23, to yield plasmid 24.

The above conventional ligations were performed in a final volume of 10 to 15 μl, where the vector to insert molar ratio was approximately 1:3. Vectors were digested with appropriate restriction enzymes, then treated with calf intestinal alkaline phosphatase, as directed by the manufacturer (New England Biolabs, Beverly, Mass.). Up to 500 ng of vector was ligated to an appropriate amount of insert in 60 mM Tris, pH 7.6, 7 mM $MgCl_2$, 10 mM DTT, 1 mM ATP, and 400 units of $T_4$ ligase, and incubated at 14° C. overnight. These ligations were used to transform *E. coli* DH10B cells (Gibco-BRL, Grand Island, N.Y.) according to the manufacturer's protocol.

Figure 5:
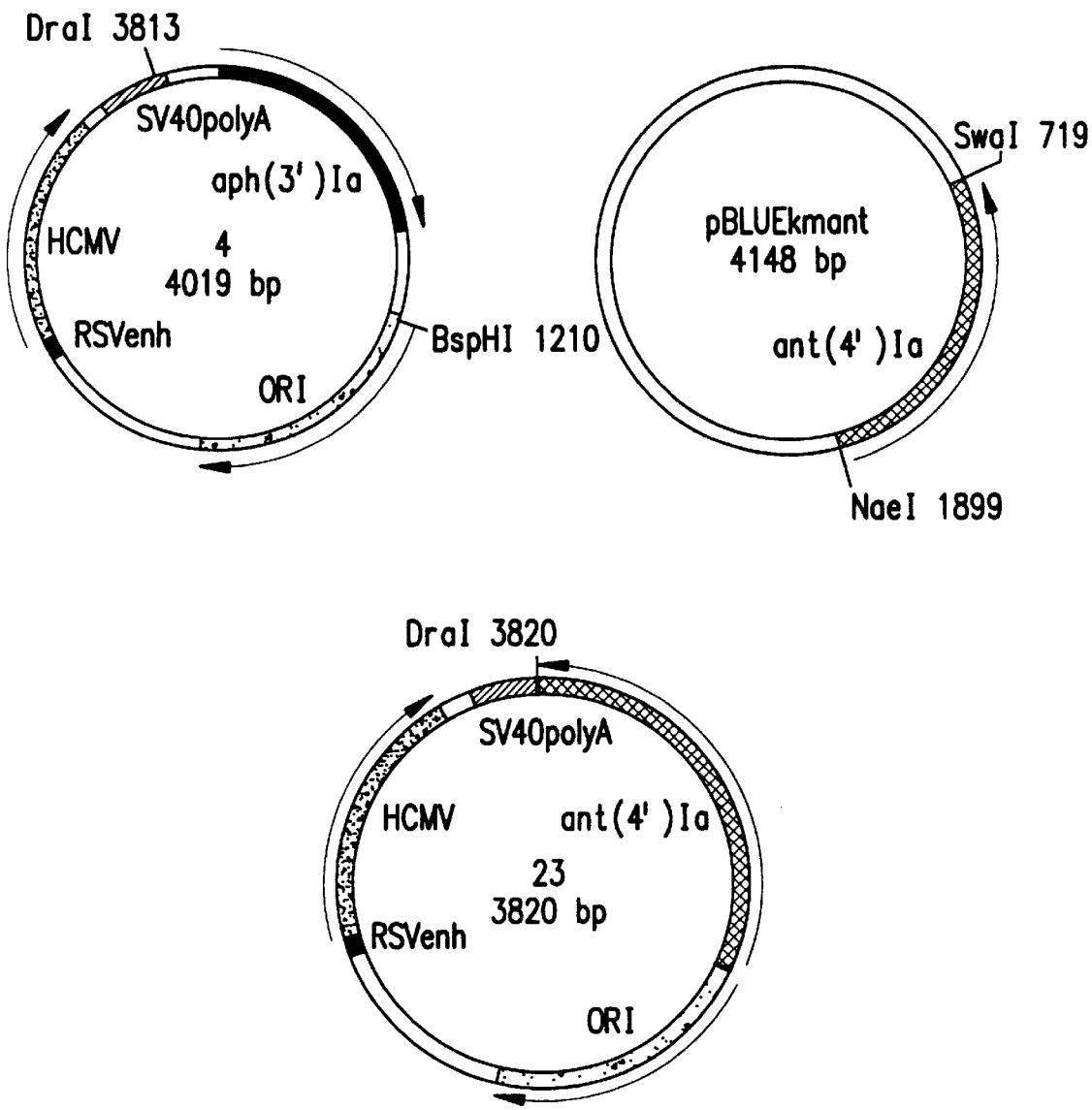
FIG. 5 shows construction of the plasmid 23 as described in Example 1. As detailed in the text, the aph(3')-Ia gene of the starting plasmid 4 was replaced with the chimeric ant(4')-Ia chimeric gene from pBLUEkm$^{ant}$. The β-lactamase gene remnant in the plasmid 4 is between the aph(3')-Ia gene and the BspHI site in the origin.

The ant(4')-Ia gene was ligated into plasmid 4 by CRC (FIG. 5). Plasmid 4 was cleaved with DraI and BspHI, and the 2.6 kb fragment generated by these enzymes was gel-purified. The 5' overhang generated by BspHI digestion was blunted with Klenow (Sambrook et al., 1989 Supra). The 1.2 kb ant(4')-Ia gene fragment was excised from pBLUEkm$^{ant}$ using NaeI and SwaI, which generate blunt ends, and the fragment was gel-purified. The desired fragments were subjected to CRC with bridge oligomers MPV73 and MPV92, and then the reaction was concentrated by precipitation and resuspended in 10 μl of TE (10 mM Tris, 7.6, 1 mM EDTA). One μl of the CRC reaction was used to transform *E. coli* DH10B cells (Gibco-BRL, Grand Island, N.Y.).

DNA Sequencing:

The Sequenase system (USB, Cleveland, Ohio) was employed for most of the sequencing performed. Approximately 50 ng of any given primer was used to prime a sequencing reaction. If a sequence could not be read by the Sequenase enzyme because of compressions, then the fmol® DNA sequencing system (Promega, Madison, Wis.) was used to resolve the discrepancies.

Cell Lines, Transfection Conditions, and Western Blots:

The human rhabdomyosarcoma cell line RD was maintained in MEM, alpha modification (JRH Biosciences, Lenexa, Kans.) supplemented with 10% fetal bovine serum, nonessential amino acids and sodium pyruvate. Cells were seeded into six-well plates, and transfected the next day with plasmid 19, plasmid 23, or plasmid 24 by the modified calcium phosphate method (Sambrook et al., 1989 Supra), or by lipofectamine according to the manufacturer's instructions (Gibco-BRL, Grand Island, N.Y.).

To determine if $HSVgD_2$ was produced by the cells, 48 hours after transfection the cells were lysed for Western blotting (Sambrook et al., 1989 Supra) . Lysates were subjected to SDS-PAGE, and electroblotted to nitrocellulose. The blot was blocked with 0.5% Tween-20 and 5% nonfat dry milk in TBS, and incubated with the anti-$HSVgD_2$ monoclonal antibody Dl-6 diluted 1:250 in the same buffer. The blot was incubated with a secondary antibody, an anti-mouse IgG polyclonal antibody conjugated to alkaline phosphatase (Jackson Immunoresearch, Bar Harbor, Me.). Binding was then detected by incubation with substrates NBT/BCIP (Promega, Madison, Wis.).

Figure 7:
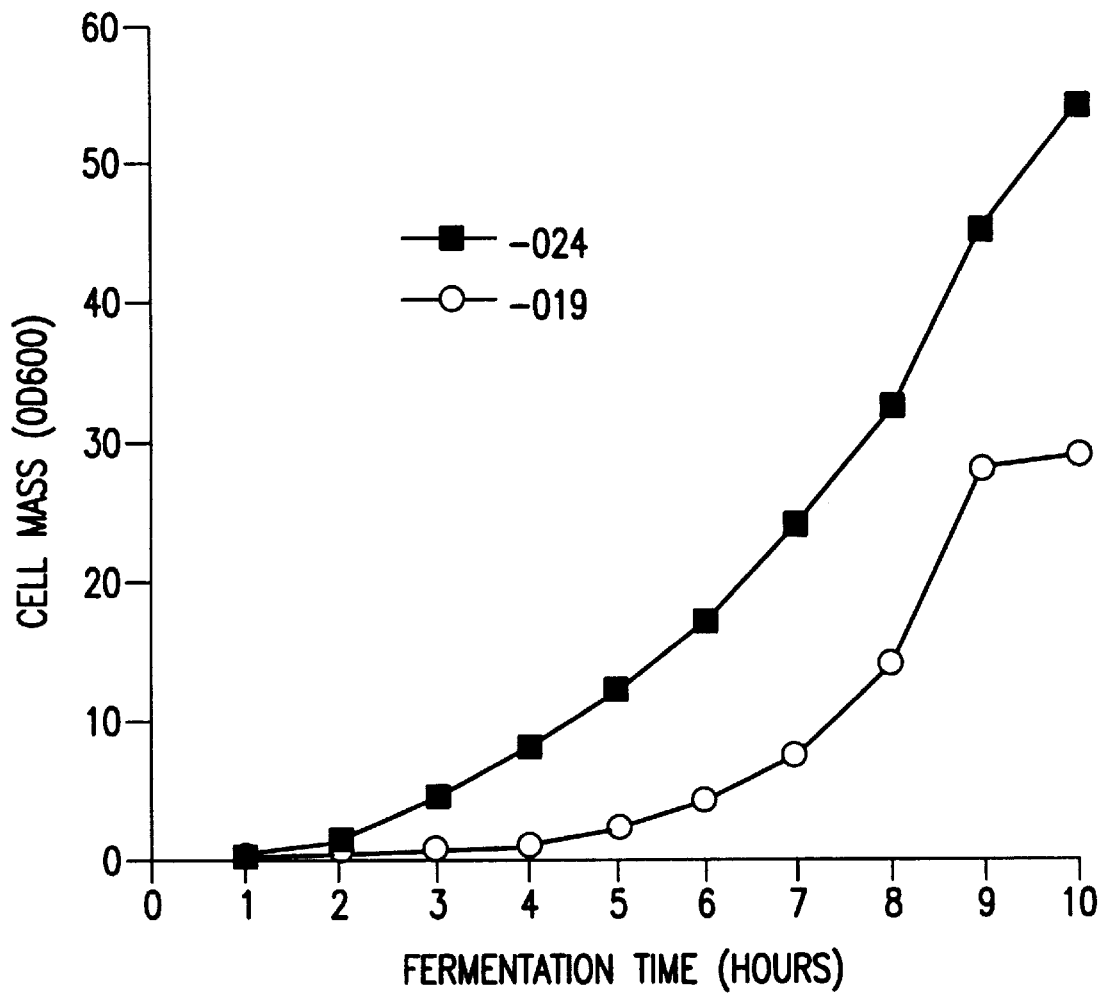
FIG. 7 shows results from experiments described in Example 1 relating to the growth of plasmid 19 and plasmid 24 in fermentation. Cell mass is measured against fermentation time for E. coli harboring either vector. FP5 is fermentation process 5.

Fermentations and Plasmid DNA Purification:

Fermentations were performed for *E. coli* DH10B containing either plasmid 19 or plasmid 24. The protocol used was fermentation process 5 (FP5). The growth profiles for either strain were very similar, and thus only one profile for each is shown in FIG. 7. Plasmid DNA was purified as described (Gayda 1995).

RESULTS AND DISCUSSION

Construction of the ant(4')-Ia Gene by PCR and CRC:

The ant(4')-Ia gene is derived from gram positive organisms. Its promoter, ribosome binding sites, and terminator are optimal for expression in such bacteria, but not for gram negative *E. coli*. The selectivity of gram negative promoters is due to the use of a single sigma factor versus the cascade of sigma factors required in gram positive organisms such as *B. subtilis*. In addition, gram negative bacterial ribosomes require that transcribed RNA contain specific signals for translation, which are lacking in RNA from gram positive organisms.

Initially, the coding region from the ant(4')-Ia gene was linked to the promoter and terminator from the aph(3')-Ia gene, which expresses well in *E. coli*. In addition, an Eco47III site within the ant(4')-Ia gene coding region needed to be eliminated for purposes of future cloning, but only a single base had to be altered, which did not change the protein sequence. PCR was used to individually amplify the aph(3')-Ia promoter, including the ribosome binding site, and the terminator sequences. The ant(4')-Ia gene coding region was likewise amplified in two pieces, with the antisense primer of the 5' fragment altering the Eco47III site.

The fragments were mixed in roughly equimolar amounts, with an excess of bridge oligomers to hybridize and join the fragments in the correct order. The fragments were subjected to CRC (FIG. 1B), and approximately 40% of the CRC reaction was then subjected to PCR. This second PCR reaction employed the two outermost primers, MPV37 and MPV44, which amplified across the entire length of the engineered gene. The PCR products were ligated into the pCR™3 vector, transformed into *E. coli*, and selected on LB ampicillin plates.

Of fifty clones selected for analysis, three were full length representations of the engineered ant(4')-Ia gene. One clone (pkm23) was fully sequenced, and found to be identical to the various input DNAs and with the correct junctions between each PCR fragment. This clone was selected for functional analysis.

The pCR™3 vector already contained a kanamycin resistance gene, so it was not possible to determine directly if ant(4')-Ia gene were functional in pkm23. The ant(4')-Ia gene insert of pkm23 was subcloned into pGEM11Zf+, a vector which only contains an ampicillin resistance gene. While the subcloning was successful, the bacteria containing pGEMkm$^{ant}$ plasmid grew only on plates containing ampicillin, not on plates containing kanamycin. Thus, the engineered ant(4')-Ia gene was not functional.

Reconstruction of the ant(4')-Ia Gene:

Closer examination of the translation initiation region of the engineered ant(4')-Ia gene suggested that it was not functional because it was not translated correctly in *E. coli*. Translation initiation regions in *E. coli* genes are characterized by a purine-rich ribosome binding sequence, called the Shine-Dalgarno box, followed 5 to 15 bases downstream by the translation initiation codon, usually the first ATG of the coding sequence. One of the many differences between gram negative and gram positive organisms is that the former almost always use ATG as the start codon, but the latter use ATG or GTG. In fact, the GTG codon is poorly recognized as the initiation codon by gram negative bacteria.

The engineered ant(4')-Ia gene contains a Shine-Dalgarno box from the aph(3')-Ia promoter, but it is followed by two potential start codons from the ant(4')-Ia coding sequence: the in-frame GTG and an out-of-frame ATG that are 5 and 9 bases downstream, respectively (FIG. 2). Only translation from the GTG would give rise to a functional enzyme, but it is unlikely to be recognized as the start codon by *E. coli* ribosomes.

Based on the above analysis, the translation initiation region was altered, from GTG AAT GGA to ATG AAC GGA. Changing the bold-faced bases does not alter the protein sequence. Again, a combination of PCR and CRC was employed to generate these mutations, as detailed in FIGS. 3A and 3B. The pGEMkm$^{ant}$ plasmid served as template, in which the promoter was amplified in one reaction, and the coding region and terminator in another reaction. The sense primer used to amplify the coding region and terminator incorporated the desired nucleotide changes. The PCR fragments were then linked by CRC, and the products were amplified by a second round of PCR using the outermost primers to amplify the entire gene. The final PCR product was cleaved at unique sites on the 5' and 3' ends, and cloned directly into pBluescript which only carries an ampicillin resistance gene. The ligations were transformed into *E. coli*, and grown on plates containing kanamycin. Twenty-two colonies were obtained, and three were sequenced in the junction region between the promoter and coding region. All three had the corrected first and second codons. The ant(4') -Ia gene of one of the three clones was then sequenced, and found to be otherwise identical to the pGEMkmant template (see FIGS. 4A and 4B). This clone is designated pBLUEkm$^{ant}$ and it contains an insert of 1200 bp, with an open reading frame of 254 amino acids, flanked by a 5' promoter sequence of 130 bp and a 3' terminator of 308 bp. Aminoglycoside Sensitivity of *E. coli* Carrying ant(4')-Ia:

A sensitivity/resistance profile to seven of the most frequently prescribed aminoglycosides was determined for *E. coli* carrying either the ant(4')-Ia gene or the aph(3')-Ia gene. The pBLUEkm$^{ant}$ and pUC4K plasmids were transformed into *E. coli* DH10B, a strain which carries a streptomycin resistance marker. The transformed strains and the host strain were tested against a series of aminoglycosides to determine their minimum inhibitory concentrations (MIC). Results are shown in Table 2, with MICs shown in μg/ml, and resistance or sensitivity indicated. All strains are resist to streptomycin as expected, but neither the ant(4')-Ia gene nor the aph(3')-Ia gene is expected to confer resistance to this antibiotic (Shaw et al., 1993). The *E. coli* strain alone is sensitive to the remaining antibiotics, providing a baseline of comparison for the bacteria carrying the plasmids with the ant(4')-Ia gene or the aph(3')-Ia gene. The data show that the ant(4')-Ia gene confers resistance to kanamycin, neomycin, and tobramycin, while the aph(3')-Ia gene confers resistance to kanamycin, neomycin, tobramycin, gentamicin and netilmicin. The most significant difference between the two genes is that the ant(4')-Ia gene is sensitive to gentamicin, an antibiotic that is still the first course of treatment for gram negative infections. Thus, the engineered ant(4')-Ia gene fulfills the requirement that it display a narrower range of activity against aminoglycosides, and should be safer for use in humans. Replacement of the aph(3')-Ia Gene in plasmid 4 with ant(4')-Ia:

The ant(4')-Ia gene was cloned by CRC into plasmid 4, to replace the aph(3')-Ia gene contained in this vector backbone. Plasmid 4 was cleaved with DraI and BspHI, which eliminates the aph(3')-Ia gene and a remnant of the β-lactamase gene left in the plasmid during its original construction. The DraI site is at the 3' end of the SV40 polyadenylation signal. Cleavage at this site removes 42 bases at one end of the element, which is not expected to affect its function. The modified clinical vector backbone resulting from this work is designated plasmid 23. Restriction analysis of plasmid 23 and sequencing of the junctions between the plasmid 4 fragment and ant(4')-Ia fragment in plasmid 23 verified that the fragments went together in the desired orientation.

In plasmid 4, aph(3')-Ia transcription was directed toward the origin. The terminator of aph(3')-Ia is rho-dependent, and rho-dependent terminators can allow a low level of readthrough transcription to occur (Darnell, J. et al., *Molecular Cell Biology*, 1986, which is incorporated herein by reference, and Miller, J. H. et al., The Operon 1980 which is incorporated herein by reference), in this case originating from the aph(3')-Ia promoter. The readthrough could result in additional RNA II transcription from the origin. Plasmid replication is, in part, a function of the binding of RNA I to RNA II (Kues, U. et al., *Microbiol. Rev.* 1989, 53:491–516, which is incorporated herein by reference), and the extra RNA II transcription might be expected to result in lower plasmid copy number per cell. To get around this potential problem, the ant(4')-Ia gene was ligated into plasmid 4 so that its transcription is directed away from the origin.

Figure 6A:
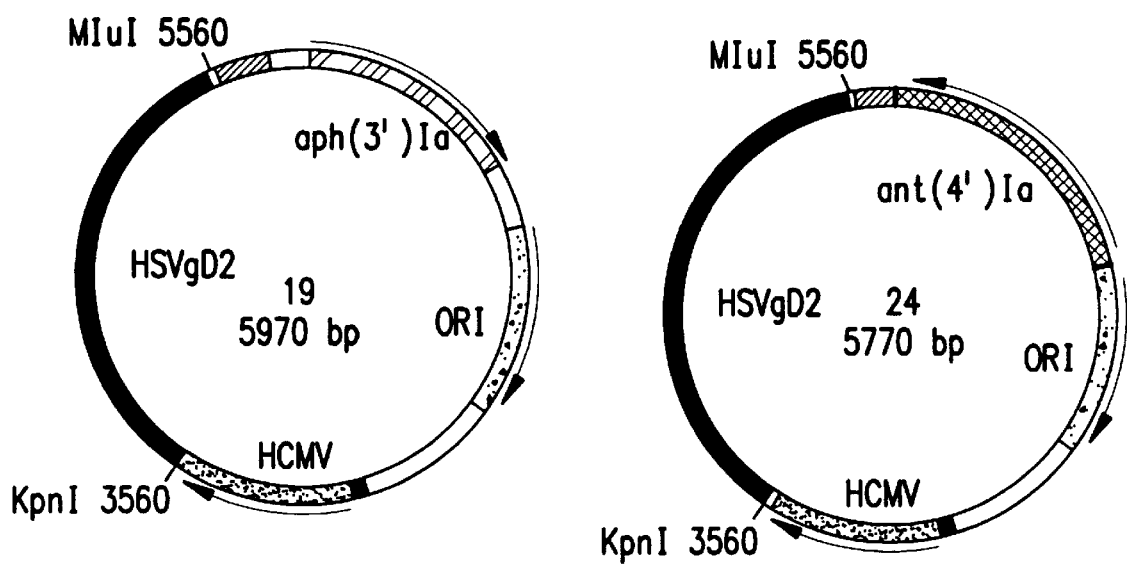
FIGS. 6A and 6B show expression of the HSV gene HSVgD$_2$ in cells transfected with the plasmid 24 as described in Example 1.

Expression of $HSVgD_2$ from plasmid 19 and plasmid 24:

When plasmid 23 was constructed, a small portion of the SV40 polyadenylation signal was deleted as described above. This deletion did not include the AATAAA sequence, or the GT-rich region required for efficient polyadenylation, but it remained possible that this deletion could adversely affect expression of the eukaryotic gene unit. To evaluate this concern, the $HSVgD_2$ gene from plasmid 19 was cloned into plasmid 23, to yield plasmid 24 (FIG. 6A). The only differences between plasmid 19 and plasmid 24 are the polyadenylation signals, and the aph(3')-Ia and ant(4')-Ia genes, respectively.

Figure 6B:
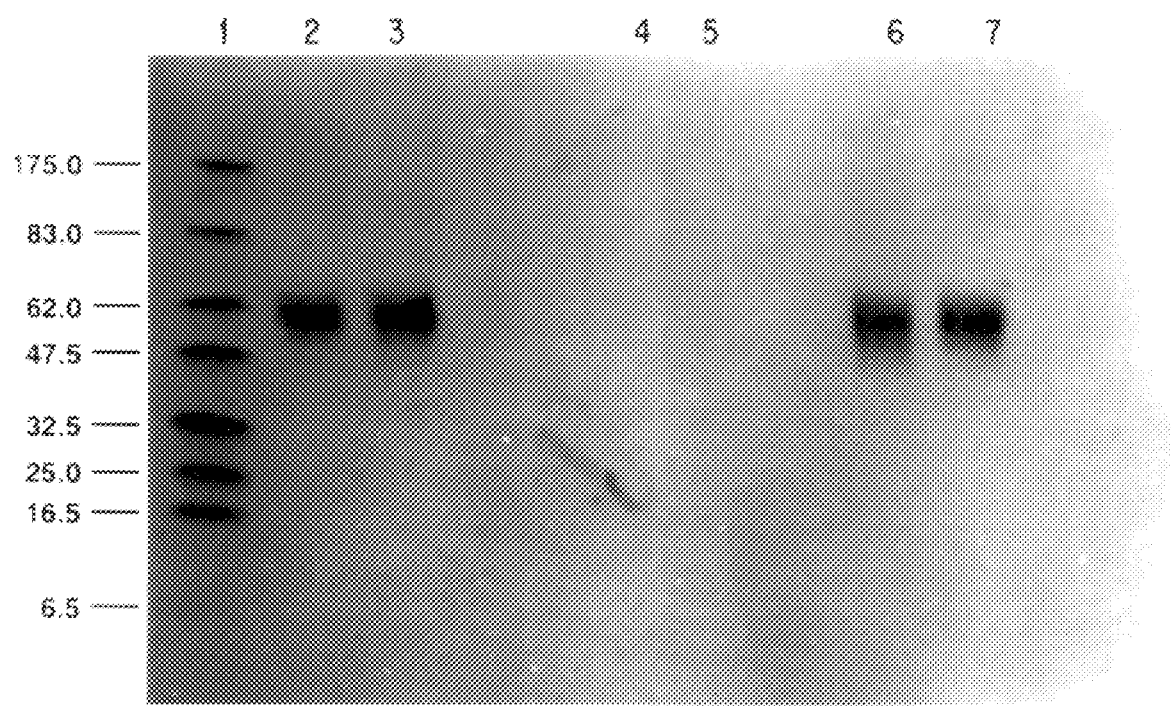

Expression studies were performed, in which RD cells were transfected with either plasmid 19, plasmid 23 or plasmid 24. Results are shown in FIG. 6B. Cells transfected with either of the vectors containing $HSVgD_2$ produce substantial amounts of the 55 kilodalton $HSVgD_2$ protein as detected by Western blot, while the lanes representing the control plasmid are negative. These data suggest that the small deletion in the SV40 polyadenylation signal does not adversely affect eukaryotic gene expression from the vector. In addition, the presence of the ant(4')-Ia gene coding sequence in the vector does not appear to affect expression from the eukaryotic promoter.

Fermentation and Plasmid Yields of Bacteria Containing plasmid 19 or plasmid 24:

To determine if the presence of the ant(4')-Ia gene coding sequence in a plasmid vector backbone would influence production of plasmid DNA, three fermentations of plasmid 24 were compared with two fermentations of plasmid 19. Each plasmid vector is in *E. coli* strain DH10B, and the same fermentation and DNA purification protocols were performed for each strain.

Representative growth curves for the two bacterial strains are shown in FIG. 7. The plasmid 24 strain grows much more rapidly than the plasmid 19 strain, and reaches nearly twice the $OD_{600}$ after ten hours of fermentation. The plasmid DNA yields for each strain were also compared (Table 3). More plasmid 24 DNA was produced than plasmid 19, but the amounts are proportional to the cell yield. Thus, bacteria containing plasmid 24 or plasmid 19 produce similar amounts of plasmid DNA, but because the plasmid 24 strain grows so much better, the yield of DNA from fermentation has improved substantially.

It is likely that the growth advantage seen with plasmid 24 is due to the biochemical activities of the ANT(4')-IA enzyme when compared with those of the APH(3')-IA enzyme. The ATP used as a phosphate donor by APH(3')-IA is limited in concentration in growing cells. Given the ability of APH(3')-IA to phosphorylate a wide range of cellular substrates, including kanamycin and water, bacteria harboring this enzyme to grow more slowly due to futile cycles of ATP generation followed by APH(3')-Ia mediated ATP breakdown.

ANT(4')-IA enzyme may have additional cellular activities beyond conferring drug resistance, including a positive effect on cell growth. It is well known that cell growth is controlled by the levels of several global growth regulators, including cyclic AMP (cAMP), leucine and glutamine. In particular, cAMP is a negative global growth regulator, in that high cellular levels of this metabolite are associated with low growth rate, while low cAMP levels are associated with a high growth rate. Since ANT(4')-IA enzyme acts by cleaving nucleotides, cAMP may serve as a substrate for the enzyme.

To assess the cAMP phosphodiesterase activity in *E. coli* alone, and in *E. coli* with plasmids carrying either aph(3')-Ia or ant(4')-Ia an experiment was done. *E. coli* with the ant(4')-Ia gene possess 320-fold more cAMP phosphodiesterase activity than *E. coli* alone, and 400-fold more activity than *E. coli* bearing aph(3')-Ia. Lower intracellular levels of cAMP may account for the improved cellular growth rate seen in *E. coli* bearing ant(4')-Ia. That is, the elevated cAMP phosphodiesterase activity seen in *E. coli* that expresses ANT(4')-IA enzyme, may leads to lower levels of cAMP which could account for higher cellular growth.

The beneficial biochemical effects of the chimeric ant(4')-Ia gene could be conferred to host cells in either of two ways. The ant(4')-Ia gene could be supplied on a plasmid, as in the case of plasmid 24. Alternatively, the ant(4')-Ia gene could be integrated into the chromosomal DNA of cells. Two examples follow. First, to generate a mammalian cell line with the ant(4')-Ia gene integrated into the chromosome, one would transfect cells with a plasmid containing ant(4')-Ia, and select for cell clones stably resistant to neomycin (neomycin, but not kanamycin, is toxic to mammalian cells, and as shown previously, ant(4')-Ia confers resistance to neomycin). Second, an *E. coli* strain with the ant(4')-Ia gene integrated into the chromosome could be generated by homologous recombination. In this case, one would insert the ant(4')-Ia gene into the center of 1–2 kb of cloned *E. coli* DNA, and use the resulting linear fragment to transform *E. coli* (C. Satishchandran, et al., 1991 *J. Bacteriol.* 172:4489–4496 incorporated herein). Kanamycin-resistant strains would be selected for and analyzed molecularly to show that the desired recombination event occurred.

CONCLUSIONS

A hybrid kanamycin resistance gene which utilizes the *E. coli* aph(3')-Ia promoter and terminator to control expression of the ant(4')-Ia coding region is described. The first and second codons of the engineered gene have been altered to ensure efficient expression of the gene. When the sensitivity spectrum of *E. coli* strains carrying ant(4')-Ia was compared with that of strains carrying aph(3')-Ia, ant(4')-Ia conferred resistance only to kanamycin, neomycin and tobramycin, while aph(3')-Ia conferred resistance to kanamycin, neomycin, tobramycin, netilmicin, and gentamicin. Thus, the engineered gene has a more restricted range of activity and represents a significant safety improvement relative to clinical vectors which employ the aph(3')-Ia gene. The vector backbones with the ant(4')-Ia gene support good expression from the eukaryotic promoter contained in the backbone. Finally, the presence of the ant(4')-Ia gene in the backbone is a manufacturing improvement, in that bacteria bearing plasmid 23-derived vectors grow significantly better and consequently produce more DNA.

TABLE 1

PRIMERS AND OLIGOMERS

| PCR PRIMERS | SEQUENCE OF PRIMERS (5' TO 3') |
|---|---|
| MPV37 | GGCCGGCCGGGGAAAGCCACGTTGTGTCTC (SEQ ID NO:5) |
| MPV38 | AACACCCCTTGTATTACTGTTTATGTAAG (SEQ ID NO:6) |
| MPV39 | GTGAATGGACCAATAATAATGACTAGAG (SEQ ID NO:7) |
| MPV40 | CGCGCTCGTCGTATAACAGATGCG (SEQ ID NO:8) |
| MPV41 | TCGGTCTTAACTGAAGCAGTTAAGC (SEQ ID NO:9) |
| MPV42 | CGTTCAAAATGGTATGCGTTTTGACAC (SEQ ID NO:10) |
| MPV43 | CAGAATTGGTTAATTGGTTGTAACACTG (SEQ ID NO:11) |
| MPV44 | ATTTAAATGGGGGCGCTGAGGTCTGCCTCG (SEQ ID NO:12) |
| MPV62 | ATGAACGGACCAATAATAATGACTAGAGAAGAAAG (SEQ ID NO:13) |
| MPV63 | CGGGATCCATTTAAATGGGGGCGCTGAGGTCTG (SEQ ID NO:14) |
| MPV64 | GCTCTAGAGGCCGGCCGGGGAAAGCCACG (SEQ ID NO:15) |
| BRIDGE OLIGOMERS | |
| MPV45 | CAGTAATACAAGGGGTGTTGTGAATGGACCAATAATAATG (SEQ ID NO:16) |
| MPV46 | GTTATACGACGAGCGCGTCGGTCTTAACTGAAGCAG (SEQ ID NO:17) |
| MPV47 | CGCATACCATTTTGAACGCAGAATTGGTTAATTGGTTG (SEQ ID NO:18) |
| MPV67 | CAGTAATACAAGGGGTGTTATGAACGGAC CAATAATAATG (SEQ ID NO:19) |
| MPV73 | CACAACGTGGCTTTCCCCGGCCCATGACCAAAATCCCTTAACGTGAG (SEQ ID NO:20) |
| MPV92 | CAGGGGGAGGTGTGGGAGGTTTTTTAAATGGGGGCGCTGAGGTCTGCC (SEQ ID NO:21) |

TABLE 2

Spectrum of Activity of ANT(4')-IA and APH(3')-IA Against Aminoglycosides

| Aminoglycoside | DH10B | DH10B/pBLUEkm$^{ant}$ | DH10B/pUC4K |
|---|---|---|---|
| kanamycin | 1.0 S | 32 R | 32 R |
| neomycin | 0.5 S | 32 R | 32 R |
| tobramycin | 1.0 S | 16 R | 8 R |
| gentamicin | 0.5 S | 0.25 S | 5 R |
| netilmicin | 0.12 S | 0.25 S | 25 R |
| streptomycin | 128 R | 128 R | 128 R |
| spectinomycin | 4.0 S | 4.0 S | 4.0 S |

TABLE 3

Yields of plasmid 19 and plasmid 24 DNA After Fermentation

|  | plasmid 19 | plasmid 24 | 24/19 |
|---|---|---|---|
| Cells (g/l) | 46 | 86 | 1.86 |
| Plasmid DNA (mg/l) | 13 | 22 | 1.69 |

---

We claim:

1. A chimeric kanamycin resistance gene comprising:
a nucleotide sequence that encodes ANT(4')-IA enzyme operably linked to a heterologous prokaryotic promoter and a heterologous prokaryotic termination sequence.

2. The chimeric kanamycin resistance gene of claim 1 wherein said nucleotide sequence that encodes ANT(4')-IA enzyme is operably linked to a promoter from an aph(3')-Ia gene and a termination sequence from an aph(3')-Ia gene.

3. The chimeric kanamycin resistance gene of claim 1 comprising the coding sequence set forth in SEQ ID NO:3.

4. The chimeric kanamycin resistance gene of claim 1 wherein said nucleotide sequence that encodes ANT(4')-IA is free of an Eco47III restriction enzyme site.

5. The chimeric kanamycin resistance gene of claim 1 further comprising a heterologous 5' untranslated sequence including a Shine-Dalgarno sequence.

6. The chimeric kanamycin resistance gene of claim 1 wherein said heterologous promoter is a promoter from an aph(3')-Ia gene.

7. The chimeric kanamycin resistance gene of claim 1 further comprising a heterologous 5' untranslated sequence including a Shine-Dalgarno sequence, wherein said heterologous promoter, said heterologous 5' untranslated sequence and said heterologous termination sequence are from an aph(3')-Ia gene.

8. A plasmid comprising a chimeric kanamycin resistance gene according to claim 1.

9. A plasmid comprising a chimeric kanamycin resistance gene according to claim 7.

10. A bacteria cell comprising a plasmid according to claim 8.

11. A bacteria cell comprising a plasmid according to claim 9.

12. A bacteria cell comprising a chimeric kanamycin resistance gene according to claim 1.

13. A bacteria cell comprising a chimeric kanamycin resistance gene according to claim 7.

14. A method of producing plasmids according to claim 8 comprising the steps of:
culturing, in media which contains kanamycin, bacteria cells that comprise said plasmids, and
isolating said plasmids from media and bacteria cell materials.

15. A method of producing plasmids according to claim 9 comprising the steps of:
culturing, in media which contains kanamycin, bacteria cells that comprise said plasmids, and
isolating said plasmids from media and bacteria cell materials.

16. A plasmid according to claim 8 further comprising a viral gene coding sequence.

17. A plasmid according to claim 9 further comprising a viral gene coding sequence.

18. A method of enhancing growth of a bacterial cell in the presence of kanamycin comprising the steps of:
introducing into said bacterial cell, a chimeric kanamycin resistance gene according to claim 1; and,
culturing said bacterial cell in media which contains kanamycin
wherein culturing said bacterial cell which comprises said chimeric kanamycin resistance gene in the presence of kanamycin results in enhanced growth of said bacterial cell.

19. The method of claim 18 wherein said chimeric gene is integrated into said cell's genome.

20. The method of claim 18 wherein said chimeric gene is a plasmid which is maintained in said cell extrachromosomally.

21. A plasmid comprising:
a bacterial origin of replication,
a composite promoter comprising the Rous sarcoma virus (RSV) enhancer in combination with the human cytomegalovirus (HCMV) intermediate early promoter,
a polylinker/cloning site for insertion of coding sequence that encodes a desired protein or immunogen,
an SV40 polyadenylation signal, and
a chimeric kanamycin resistance gene according to claim 1.

22. The plasmid of claim 21 further comprising the coding sequence of herpes simplex virus gene HSVgD$_2$ inserted into said polylinker/cloning site and operably linked to said composite promoter and polyadenylation signal.

23. The plasmid of claim 21 further comprising the coding sequence of human immunodeficiency virus genes env, rev, truncated nef, truncated vpu and human immunodeficiency virus rev responsive element (rre) inserted into said polylinker/cloning site and operably linked to said composite promoter and polyadenylation signal.

24. The plasmid of claim 16 wherein said viral gene coding sequence is a herpes simplex virus gene coding sequence or a human immunodeficiency gene coding sequence.

25. The plasmid of claim 24 wherein said viral gene coding sequence is a herpes simplex virus gene coding sequence.

26. The plasmid of claim 24 wherein said viral gene coding sequence is a human immunodeficiency gene coding sequence.

27. The plasmid of claim 17 wherein said viral gene coding sequence is a herpes simplex virus gene coding sequence or a human immunodeficiency gene coding sequence.

28. The plasmid of claim 27 wherein said viral gene coding sequence is a herpes simplex virus gene coding sequence.

29. The plasmid of claim 27 wherein said viral gene coding sequence is a human immunodeficiency gene coding sequence.

* * * * *

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 9 base pairs
        ( B ) TYPE: nucleic acid
        ( C ) STRANDEDNESS: both
        ( D ) TOPOLOGY: both ( i i ) MOLECULE TYPE: DNA ( x i ) SEQUENCE DESCRIPTION: SEQ ID NO:1:

GTGAATGGA 9

(2) INFORMATION FOR SEQ ID NO:2:

( i ) SEQUENCE CHARACTERISTICS:
        ( A ) LENGTH: 9 base pairs
        ( B ) TYPE: nucleic acid
        ( C ) STRANDEDNESS: both
        ( D ) TOPOLOGY: both ( i i ) MOLECULE TYPE: DNA ( x i ) SEQUENCE DESCRIPTION: SEQ ID NO:2:

ATGAACGGA 9

(2) INFORMATION FOR SEQ ID NO:3:

( i ) SEQUENCE CHARACTERISTICS:
        ( A ) LENGTH: 1200 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 131..892

( x i ) SEQUENCE DESCRIPTION: SEQ ID NO:3:

```
GCTCTAGAGG CCGGCCGGGG AAAGCCACGT TGTGTCTCAA AATCTCTGAT GTTACATTGC    60

ACAAGATAAA AATATATCAT CATGAACAAT AAAACTGTCT GCTTACATAA ACAGTAATAC   120

AAGGGGTGTT ATG AAC GGA CCA ATA ATA ATG ACT AGA GAA GAA AGA ATG   169
              Met Asn Gly Pro Ile Ile Met Thr Arg Glu Glu Arg Met
                1               5                  10

AAG ATT GTT CAT GAA ATT AAG GAA CGA ATA TTG GAT AAA TAT GGG GAT    217
Lys Ile Val His Glu Ile Lys Glu Arg Ile Leu Asp Lys Tyr Gly Asp
    15              20                  25

GAT GTT AAG GCT ATT GGT GTT TAT GGC TCT CTT GGT CGT CAG ACT GAT    265
Asp Val Lys Ala Ile Gly Val Tyr Gly Ser Leu Gly Arg Gln Thr Asp
30              35                  40                      45

GGG CCC TAT TCG GAT ATT GAG ATG ATG TGT GTC ATG TCA ACA GAG GAA    313
Gly Pro Tyr Ser Asp Ile Glu Met Met Cys Val Met Ser Thr Glu Glu
                50                  55                  60

GCA GAG TTC AGC CAT GAA TGG ACA ACC GGT GAG TGG AAG GTG GAA GTG    361
Ala Glu Phe Ser His Glu Trp Thr Thr Gly Glu Trp Lys Val Glu Val
            65                  70                  75

AAT TTT GAT AGC GAA GAG ATT CTA CTA GAT TAT GCA TCT CAG GTG GAA    409
Asn Phe Asp Ser Glu Glu Ile Leu Leu Asp Tyr Ala Ser Gln Val Glu
        80                  85                  90

TCA GAT TGG CCG CTT ACA CAT GGT CAA TTT TTC TCT ATT TTG CCG ATT    457
Ser Asp Trp Pro Leu Thr His Gly Gln Phe Phe Ser Ile Leu Pro Ile
    95                 100                 105

TAT GAT TCA GGT GGA TAC TTA GAG AAA GTG TAT CAA ACT GCT AAA TCG    505
Tyr Asp Ser Gly Gly Tyr Leu Glu Lys Val Tyr Gln Thr Ala Lys Ser
110                 115                 120                 125

GTA GAA GCC CAA ACG TTC CAC GAT GCG ATT TGT GCC CTT ATC GTA GAA    553
Val Glu Ala Gln Thr Phe His Asp Ala Ile Cys Ala Leu Ile Val Glu
                130                 135                 140

GAG CTG TTT GAA TAT GCA GGC AAA TGG CGT AAT ATT CGT GTG CAA GGA    601
Glu Leu Phe Glu Tyr Ala Gly Lys Trp Arg Asn Ile Arg Val Gln Gly
            145                 150                 155
```

```
CCG ACA ACA TTT CTA CCA TCC TTG ACT GTA CAG GTA GCA ATG GCA GGT      649
Pro Thr Thr Phe Leu Pro Ser Leu Thr Val Gln Val Ala Met Ala Gly
        160                 165                 170

GCC ATG TTG ATT GGT CTG CAT CAT CGC ATC TGT TAT ACG ACG AGC GCG      697
Ala Met Leu Ile Gly Leu His His Arg Ile Cys Tyr Thr Thr Ser Ala
        175                 180                 185

TCG GTC TTA ACT GAA GCA GTT AAG CAA TCA GAT CTT CCT TCA GGT TAT      745
Ser Val Leu Thr Glu Ala Val Lys Gln Ser Asp Leu Pro Ser Gly Tyr
190                 195                 200                 205

GAC CAT CTG TGC CAG TTC GTA ATG TCT GGT CAA CTT TCC GAC TCT GAG      793
Asp His Leu Cys Gln Phe Val Met Ser Gly Gln Leu Ser Asp Ser Glu
                210                 215                 220

AAA CTT CTG GAA TCG CTA GAG AAT TTC TGG AAT GGG ATT CAG GAG TGG      841
Lys Leu Leu Glu Ser Leu Glu Asn Phe Trp Asn Gly Ile Gln Glu Trp
            225                 230                 235

ACA GAA CGA CAC GGA TAT ATA GTG GAT GTG TCA AAA CGC ATA CCA TTT      889
Thr Glu Arg His Gly Tyr Ile Val Asp Val Ser Lys Arg Ile Pro Phe
        240                 245                 250

TGA ACGCAGAATT GGTTAATTGG TTGTAACACT GGCAGAGCAT TACGCTGACT           942
 *

TGACGGGACG GCGGCTTTGT TGAATAAATC GAACTTTTGC TGAGTTGAAG GATCAGAT     1002

CGCATCTTCC CGACAACGCA GACCGTTCCG TGGCAAAGCA AAAGTTCAAA ATCACCAA     1062

GGTCCACCTA CAACAAAGCT CTCATCAACC GTGGCTCCCT CACTTTCTGG CTGGATGA     1122

GGGCGATTCA GGCCTGGTAT GAGTCAGCAA CACCTTCTTC ACGAGGCAGA CCTCAGCG     1182

CCCATTTAAA TGGATCCG                                                 1200
```

( 2 ) INFORMATION FOR SEQ ID NO:4:

( i ) SEQUENCE CHARACTERISTICS:
        ( A ) LENGTH: 253 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Asn Gly Pro Ile Ile Met Thr Arg Glu Glu Arg Met Lys Ile Val
 1               5                  10                  15

His Glu Ile Lys Glu Arg Ile Leu Asp Lys Tyr Gly Asp Val Lys
                20                  25                  30

Ala Ile Gly Val Tyr Gly Ser Leu Gly Arg Gln Thr Asp Gly Pro Tyr
            35                  40                  45

Ser Asp Ile Glu Met Met Cys Val Met Ser Thr Glu Glu Ala Glu Phe
        50                  55                  60

Ser His Glu Trp Thr Thr Gly Glu Trp Lys Val Glu Val Asn Phe Asp
65                  70                  75                  80

Ser Glu Glu Ile Leu Leu Asp Tyr Ala Ser Gln Val Glu Ser Asp Trp
                85                  90                  95

Pro Leu Thr His Gly Gln Phe Phe Ser Ile Leu Pro Ile Tyr Asp Ser
            100                 105                 110

Gly Gly Tyr Leu Glu Lys Val Tyr Gln Thr Ala Lys Ser Val Glu Ala
        115                 120                 125

Gln Thr Phe His Asp Ala Ile Cys Ala Leu Ile Val Glu Glu Leu Phe
    130                 135                 140

Glu Tyr Ala Gly Lys Trp Arg Asn Ile Arg Val Gln Gly Pro Thr Thr
145                 150                 155                 160
```

| | | | | | | | | | | | | | | | |
|---|---|---|---|---|---|---|---|---|---|---|---|---|---|---|---|
| Phe | Leu | Pro | Ser | Leu<br>165 | Thr | Val | Gln | Val | Ala<br>170 | Met | Ala | Gly | Ala | Met<br>175 | Leu |
| Ile | Gly | Leu | His<br>180 | His | Arg | Ile | Cys | Tyr<br>185 | Thr | Thr | Ser | Ala | Ser<br>190 | Val | Leu |
| Thr | Glu | Ala<br>195 | Val | Lys | Gln | Ser | Asp<br>200 | Leu | Pro | Ser | Gly | Tyr<br>205 | Asp | His | Leu |
| Cys | Gln<br>210 | Phe | Val | Met | Ser | Gly<br>215 | Gln | Leu | Ser | Asp | Ser<br>220 | Glu | Lys | Leu | Leu |
| Glu<br>225 | Ser | Leu | Glu | Asn | Phe<br>230 | Trp | Asn | Gly | Ile | Gln<br>235 | Glu | Trp | Thr | Glu | Arg<br>240 |
| His | Gly | Tyr | Ile | Val<br>245 | Asp | Val | Ser | Lys | Arg<br>250 | Ile | Pro | Phe | | | |

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

GGCCGGCCGG GGAAAGCCAC GTTGTGTCTC    30

( 2 ) INFORMATION FOR SEQ ID NO:6:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

AACACCCCTT GTATTACTGT TTATGTAAG    29

( 2 ) INFORMATION FOR SEQ ID NO:7:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

GTGAATGGAC CAATAATAAT GACTAGAG    28

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

CGCGCTCGTC GTATAACAGA TGCG    24

( 2 ) INFORMATION FOR SEQ ID NO:9:

( i ) SEQUENCE CHARACTERISTICS:
   ( A ) LENGTH: 25 base pairs
   ( B ) TYPE: nucleic acid
   ( C ) STRANDEDNESS: single
   ( D ) TOPOLOGY: linear ( i i ) MOLECULE TYPE: DNA ( x i ) SEQUENCE DESCRIPTION: SEQ ID NO:9:

TCGGTCTTAA CTGAAGCAGT TAAGC 25

( 2 ) INFORMATION FOR SEQ ID NO:10:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:10:

CGTTCAAAAT GGTATGCGTT TTGACAC 27

( 2 ) INFORMATION FOR SEQ ID NO:11:

( i ) SEQUENCE CHARACTERISTICS:
      ( A ) LENGTH: 28 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:11:

CAGAATTGGT TAATTGGTTG TAACACTG 28

( 2 ) INFORMATION FOR SEQ ID NO:12:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:12:

ATTTAAATGG GGGCGCTGAG GTCTGCCTCG 30

( 2 ) INFORMATION FOR SEQ ID NO:13:

( i ) SEQUENCE CHARACTERISTICS:
      ( A ) LENGTH: 35 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:13:

ATGAACGGAC CAATAATAAT GACTAGAGAA GAAAG 35

( 2 ) INFORMATION FOR SEQ ID NO:14:

( i ) SEQUENCE CHARACTERISTICS:
      ( A ) LENGTH: 33 base pairs
      ( B ) TYPE: nucleic acid
      ( C ) STRANDEDNESS: single ( D ) TOPOLOGY: linear ( i i ) MOLECULE TYPE: DNA ( x i ) SEQUENCE DESCRIPTION: SEQ ID NO:14:

CGGGATCCAT TTAAATGGGG GCGCTGAGGT CTG                33

( 2 ) INFORMATION FOR SEQ ID NO:15:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

GCTCTAGAGG CCGGCCGGGG AAAGCCACG                    29

( 2 ) INFORMATION FOR SEQ ID NO:16:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

CAGTAATACA AGGGGTGTTG TGAATGGACC AATAATAATG        40

( 2 ) INFORMATION FOR SEQ ID NO:17:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

GTTATACGAC GAGCGCGTCG GTCTTAACTG AAGCAG            36

( 2 ) INFORMATION FOR SEQ ID NO:18:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

CGCATACCAT TTTGAACGCA GAATTGGTTA ATTGGTTG          38

( 2 ) INFORMATION FOR SEQ ID NO:19:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

```
        CAGTAATACA AGGGGTGTTA TGAACGGACC AATAATAATG                    40
```

( 2 ) INFORMATION FOR SEQ ID NO:20:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

```
        CACAACGTGG CTTTCCCCGG CCCATGACCA AAATCCCTTA ACGTGAG            47
```

( 2 ) INFORMATION FOR SEQ ID NO:21:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

```
        CAGGGGAGG TGTGGGAGGT TTTTAAATG GGGGCGCTGA GGTCTGCC             48
```

( 2 ) INFORMATION FOR SEQ ID NO:22:

( i ) SEQUENCE CHARACTERISTICS:
        ( A ) LENGTH: 35 base pairs
        ( B ) TYPE: nucleic acid
        ( C ) STRANDEDNESS: both
        ( D ) TOPOLOGY: both ( i i ) MOLECULE TYPE: cDNA ( x i ) SEQUENCE DESCRIPTION: SEQ ID NO:22:

```
        CAGTAATACA AGGGGTGTT GTG AAT GGA CCA ATA A                     35
                             Met Asn Gly Pro Ile
                              1                5
```

( 2 ) INFORMATION FOR SEQ ID NO:23:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

```
        Met Asn Gly Pro Ile
         1               5
```

( 2 ) INFORMATION FOR SEQ ID NO:24:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: both ( i i ) MOLECULE TYPE: cDNA ( x i ) SEQUENCE DESCRIPTION: SEQ ID NO:24:

```
        ATG GAC CAA TAA                                                12
        Met Asp Gln *
```

(2) INFORMATION FOR SEQ ID NO:25:

(i) SEQUENCE CHARACTERISTICS:
        (A) LENGTH: 3 amino acids
        (B) TYPE: amino acid
        (D) TOPOLOGY: linear (ii) MOLECULE TYPE: protein (xi) SEQUENCE DESCRIPTION: SEQ ID NO:25:

Met Asp Gln
    1